United States Patent
Preuss et al.

(10) Patent No.: US 9,089,429 B2
(45) Date of Patent: Jul. 28, 2015

(54) ASYMMETRIC FORMATION OF SOCKETS AND/OR SOCKET INSERTS FOR THE MANIPULATION AND SUPRESSION OF NATURAL FREQUENCIES

(75) Inventors: Roman Preuss, Leinf-Echterdingen (DE); Thomas Pandorf, Esslingen-Zell (DE); Patricie Merkert, Kirchheim u. Teck (DE); Heike Idink, Esslingen (DE); Martin Dietrich, Potenitz (DE)

(73) Assignee: CeramTec GmbH, Plochingen (DE)

( * ) Notice: Subject to any disclaimer, the term of this patent is extended or adjusted under 35 U.S.C. 154(b) by 1308 days.

(21) Appl. No.: 12/375,699

(22) PCT Filed: Aug. 6, 2007

(86) PCT No.: PCT/EP2007/058123
§ 371 (c)(1),
(2), (4) Date: May 19, 2009

(87) PCT Pub. No.: WO2008/015285
PCT Pub. Date: Feb. 7, 2008

(65) Prior Publication Data
US 2009/0259318 A1    Oct. 15, 2009

(30) Foreign Application Priority Data

Aug. 4, 2006   (DE) .......................... 10 2006 036 928
Jul. 6, 2007   (DE) .......................... 10 2007 031 666

(51) Int. Cl.
*A61F 2/32*    (2006.01)
*A61F 2/34*    (2006.01)
(Continued)

(52) U.S. Cl.
CPC ............... *A61F 2/34* (2013.01); *A61F 2/30721* (2013.01); *A61F 2/32* (2013.01); *A61F 2/36* (2013.01); *A61F 2/3662* (2013.01); *A61F 2002/30004* (2013.01); *A61F 2002/30014* (2013.01); *A61F 2002/30158* (2013.01); *A61F 2002/30324* (2013.01); *A61F 2002/30563* (2013.01); *A61F 2002/30616* (2013.01); *A61F 2002/30695* (2013.01); *A61F 2002/30733* (2013.01);
(Continued)

(58) Field of Classification Search
CPC ....................................................... A61F 2/32
USPC .......... 623/11.11, 16.11, 18.11, 22.11, 22.21, 623/22.22, 22.24
See application file for complete search history.

(56) References Cited

U.S. PATENT DOCUMENTS

| 5,571,198 A | 11/1996 | Drucker et al. |
| 6,319,285 B1 | 11/2001 | Chamier et al. |

(Continued)

FOREIGN PATENT DOCUMENTS

| DE | 195 32 898 A1 | 3/1997 |
| DE | 197 55 536 A1 | 6/1999 |

(Continued)

*Primary Examiner* — Thomas J Sweet
*Assistant Examiner* — Matthew Schall
(74) *Attorney, Agent, or Firm* — Norton Rose Fulbright US LLP

(57) ABSTRACT

A socket or socket insert for a hip joint prosthesis, the shaft of which can be coupled with a ball head which in turn can be inserted in a rotatable manner in the hemispherical recess of the socket insert wherein the shaft can be implanted in the femur and the socket insert can be implanted directly or via a hip socket in the pelvic bone. To avoid squeaking, the socket and/or the socket insert are asymmetrically in their inner or outer geometries.

23 Claims, 4 Drawing Sheets

Figure 1:
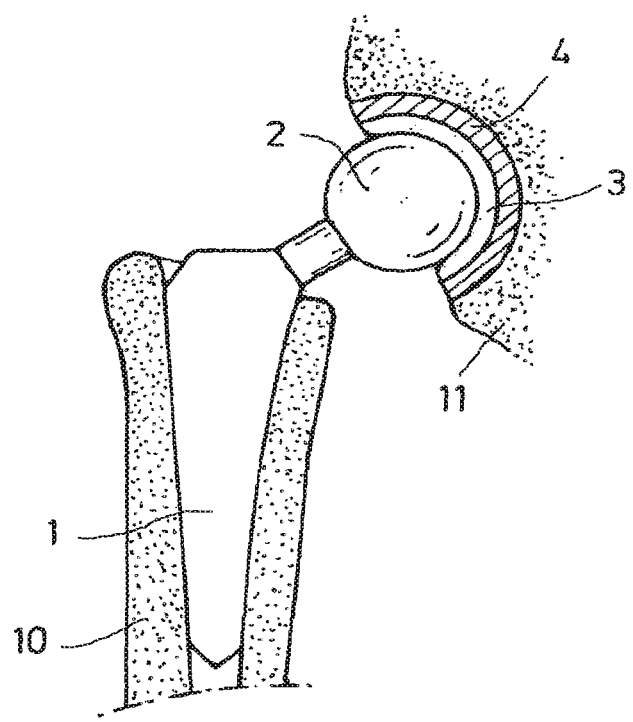

(51) Int. Cl.
*A61F 2/30* (2006.01)
*A61F 2/36* (2006.01)

(52) U.S. Cl.
CPC ... *A61F2002/3401* (2013.01); *A61F 2002/344* (2013.01); *A61F 2002/3441* (2013.01); *A61F 2002/365* (2013.01); *A61F 2002/3611* (2013.01); *A61F 2002/3625* (2013.01); *A61F 2230/0026* (2013.01); *A61F 2250/0014* (2013.01); *A61F 2250/0018* (2013.01); *A61F 2250/0036* (2013.01); *A61F 2250/0075* (2013.01)

(56) References Cited

U.S. PATENT DOCUMENTS

| | | | |
|---|---|---|---|
| 6,537,321 | B1 | 3/2003 | Horber |
| 2003/0135281 | A1 | 7/2003 | Hanssen |
| 2005/0240276 | A1 | 10/2005 | Shea et al. |
| 2006/0167556 | A1 | 7/2006 | Lazennec et al. |

FOREIGN PATENT DOCUMENTS

| | | |
|---|---|---|
| FR | 2 786 390 A | 6/2000 |
| WO | WO 03/092557 A | 11/2003 |
| WO | WO 2005/087141 A | 9/2005 |

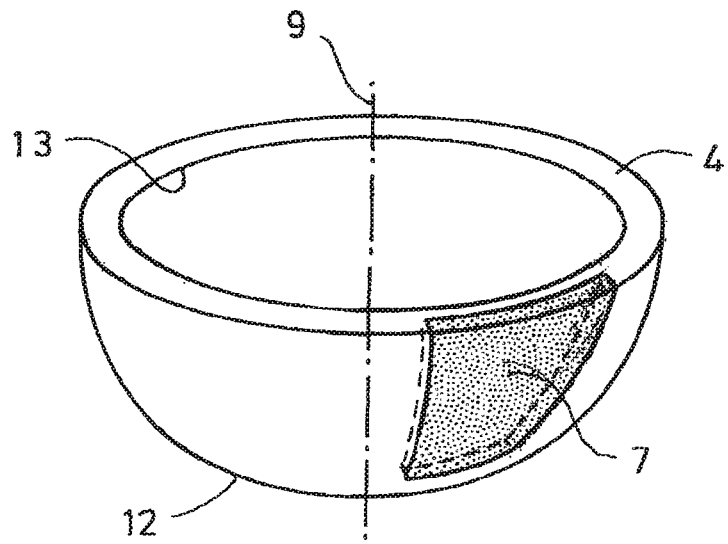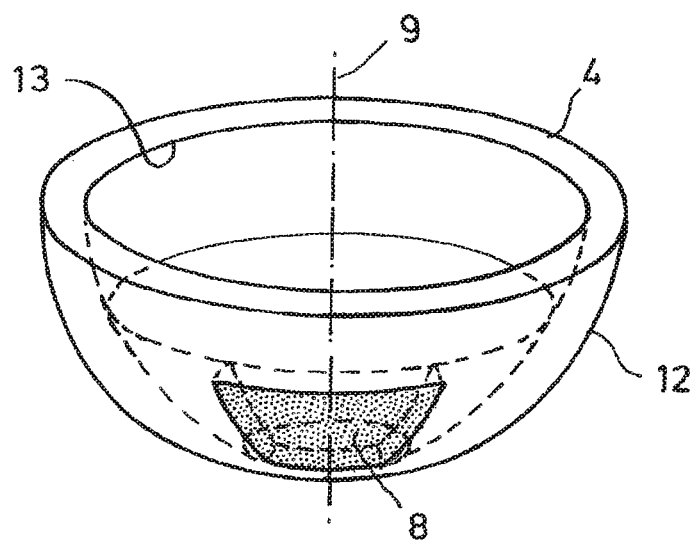

ASYMMETRIC FORMATION OF SOCKETS AND/OR SOCKET INSERTS FOR THE MANIPULATION AND SUPRESSION OF NATURAL FREQUENCIES

This application is a §371 of PCT/EP2007/058123 filed Aug. 6, 2007, which claims priority from DE 10 2006 036 928.9 filed Aug. 4, 2006 and DE 10 2007 031 666.8 filed Jul. 6, 2007.

The invention relates to a socket and/or socket insert for a hip-joint prosthesis, whose shaft can be coupled with a ball head which in turn can be inserted in a rotatable manner in the hemispherical recess of the socket insert, wherein the shaft can be implanted into the femur, and the socket insert can be implanted directly or by way of a hip socket into the pelvic bone.

PRIOR ART

A plurality of prosthetic systems for replacing a natural hip joint exist on the market. As a rule, these consist of a shaft 1 coupled with a ball head 2 and of a hip socket 4 coupled with a socket insert 3. The shaft 1 and the hip socket 4 are connected to the body as a result of growing into the femur and pelvic bone respectively and are carriers for the ball head 2 and socket insert 3 respectively. The ball head 2 is rotatably mounted in the hemispherical recess of the socket insert 3—degree of freedom: 1 (see FIG. 1).

During the articulation of the ball head in the hemispherical recess of the socket insert, for various reasons and in particular when materials of high levels of hardness are used for the ball head and socket insert (e.g. metal alloys, ceramic materials), undesirable solid-body friction can occur between the sliding partners. In this case, different phenomena can result, the consequence of which can be a resonance behaviour of the components involved and thus a development of noise, so-called squeaking. Three phenomena are briefly described in the following.

1. Depending on the material pairing, surface structure and relative speed of the two friction partners, during the movement under the effect of solid-body friction a so-called stick-slip effect can occur. This means that the quasi-continuous movement of the ball head in the hemispherical recess, when looked at closely, is made up of many temporally very short movement cycles—in each case a short movement directly followed by sudden stoppage and in turn sudden movement. This stick-slip effect is caused by constant alternation of static and sliding friction.

The vibrations emitted in consequence of the occurrence of the stick-slip effect act as excitation and lead to the vibration of the individual components of the artificial joint. If one or more of the characteristic frequencies of the components then lies/lie in the audible spectrum (approximately 16-20000 Hz), it/they can be perceived acoustically by the patient as the carrier of the artificial hip joint, for example in the form of the so-called squeaking. This is undesirable for the patient, is possibly also perceived in his surroundings and, if applicable, leads to a considerable personal restriction.

2. In consequence of frequently repeated movement patterns and also the occurrence of micro-separation (brief split of the tribological system ball-head/insert during a movement cycle), the formation of stripe wear on the ball head or the insert respectively, the development of striped wear patterns that have a certain regularity over the length of the stripe, can result. If the ball head is moved under specific individual conditions (posture, sequence of movements) relative to the insert and with contact between the components in the region of the stripe-wear zone, this can lead to self-excited vibration. If this excitation lies in the range of the characteristic frequencies of the systems involved, this leads to the development of characteristic forms and to the production of noise. If one or more of the characteristic frequencies of the components then lies/lie in the audible spectrum (approximately 16-20000 Hz), it/they can be perceived acoustically by the patient as the carrier of the artificial hip joint, for example in the form of the so-called squeaking.

3. After the insertion of artificial hip joints, in particular in the case of extreme socket positions, a contact between the metal shaft and the metal socket or between the metal shaft and the ceramic insert (another expression for socket insert) can result. If this contact does not take place point by point, but as a result of corresponding leg movement over an angle so that a "drag" of the metal shaft over the socket/insert results, this can lead to self-excited vibration. If this excitation lies in the range of the characteristic frequencies of the systems involved, this leads to the development of characteristic forms and to the production of noise. If one or more of the characteristic frequencies of the components then lies/lie in the audible spectrum (approximately 16-20000 Hz), it/they can be perceived acoustically by the patient as the carrier of the artificial hip joint, for example in the form of the so-called squeaking.

The underlying object of the invention is to develop further a socket and/or a socket insert according to the preamble of claim 1 in such a way that no squeaking occurs.

The terms socket and hip socket denote the same item and are interchangeable.

This object is achieved in that the socket and/or the socket insert are/is formed asymmetrically in its outer and/or inner geometry and/or material composition.

As a result of the specific asymmetrical formation of the socket and/or of the socket insert, the development of characteristic forms of the socket and/or of the socket insert can be prevented and the manifestation of vibrations in the components in the acoustically perceptible frequency range can be significantly damped. The asymmetry of the socket and/or of the socket insert that has been proposed can be achieved in this case by various measures, which can be combined with each other as desired:

- in the form of an asymmetrical outer geometry in all three directions in space (cross-sectional area and also longitudinal axis),
- in the form of an asymmetrical inner geometry in all three directions in space (cross-sectional area and also longitudinal axis), as well as by
- asymmetrical composition of the socket and/or socket insert out of materials with differing rigidities and damping properties.

In an inventive development, the axes of symmetry of the inner and outer geometry of the socket and/or of the socket insert are displaced in parallel. As a result of parallel displacement of the axes of symmetry of the inner and outer geometry, a rotationally symmetrical component no longer exists. There is just simple symmetry with regard to a plane.

In addition, the axis of symmetry of the inner geometry is preferably tilted in relation to the axis of symmetry of the outer geometry by an angle $\alpha$, as a result of which an asymmetrical socket and/or socket insert exists with corresponding effects upon the vibration behaviour.

In an inventive development, the angle $\alpha$ lies in the range of 5 degrees $< \alpha <$ 25 degrees.

In an alternative embodiment, the socket and/or the socket insert are/is composed of materials of differing rigidities and damping properties.

In another development of the invention, partial elements of materials with differing rigidity and damping properties are arranged in the socket and/or in the socket insert.

The socket and/or the socket insert can also have recesses on the inner and/or outer geometry.

Advantageously, the rigidities and/or damping properties and/or the material are configured differently along the axis of symmetry of the socket and/or the socket-insert axis.

The prior art and the invention are explained in greater detail in the following with the aid of figures.

FIG. 1 shows the prior art. A hip prosthesis as a rule consists of a shaft 1 coupled with a ball head 2 and of a hip socket 4 coupled with a socket insert 3. The shaft 1 and the hip socket 4 are connected to the body of the patient as a result of growing into the femur 10 and pelvic bone 11 respectively and are carriers for the ball head 2 and socket insert 3 respectively. The ball head 2 is rotatably mounted in the hemispherical recess of the socket insert 3.

Figure 2:
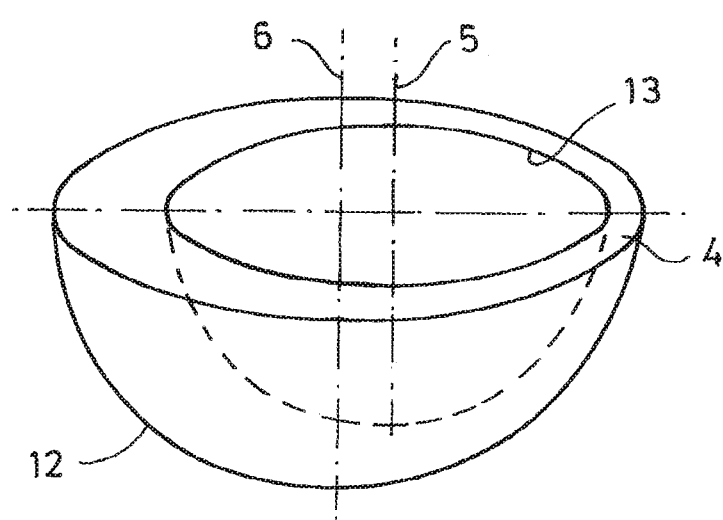

FIG. 2 shows a socket 4 in accordance with the invention with an outer geometry 12 that is adapted to the implantation into the pelvic bone 11 (see FIG. 1). The inner geometry 13 of the socket 4 is adapted to the outer geometry of the socket insert 3. In order to avoid squeaking the axes of symmetry 5, 6 of the inner geometry 13 and the outer geometry 12 of the socket 4 are displaced in parallel. As a result of this parallel displacement of the axes of symmetry 5, 6 of the inner geometry 13 and the outer geometry 12 of the socket 4 a rotationally symmetrical component no longer exists. There is just simple symmetry with regard to a plane.

Figure 3:
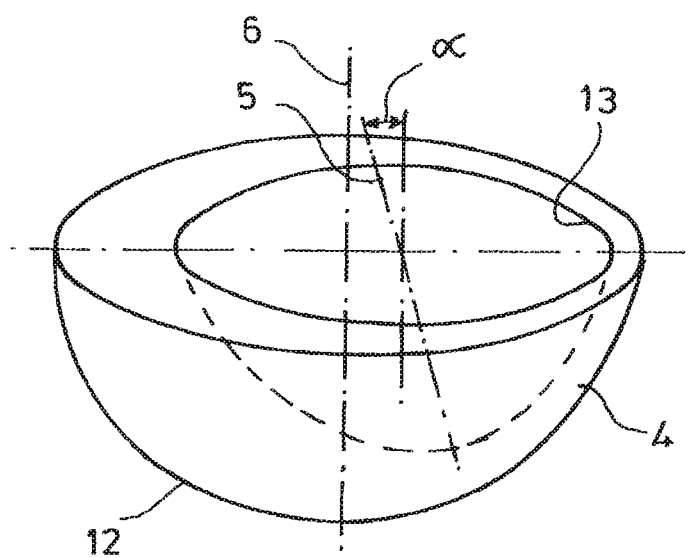

If in addition the axis of symmetry 5 of the inner geometry 13 is tilted further in relation to the axis of symmetry 6 of the outer geometry 12, an asymmetrical socket 4 exists—with corresponding effects upon the vibration behaviour. See FIG. 3 regarding this. The same reference numerals also denote the same item.

FIG. 4 shows a socket 4 in accordance with the invention in which partial elements 7 consisting of materials with differing rigidity and damping properties are arranged. As a result of the composition of the socket 4 of materials with differing rigidity and damping properties or as a result of insertion of a partial element 7 into the existing geometry of the socket 4 that consists of a material differing in terms of rigidity and damping property from that of the existing socket 4, the squeaking is eliminated.

In the extreme case, the same effect is achieved by means of a recess 8 in the socket 4, that is, the geometry becomes very asymmetrical or an element with greatly differing material properties is "inserted" (see FIG. 5).

In the case of the sockets 4 that are shown in FIGS. 4 and 5, the axis of symmetry of the inner geometry 13 and the axis of symmetry of the outer geometry 12 coincide and form a common socket axis 9.

Figure 6:
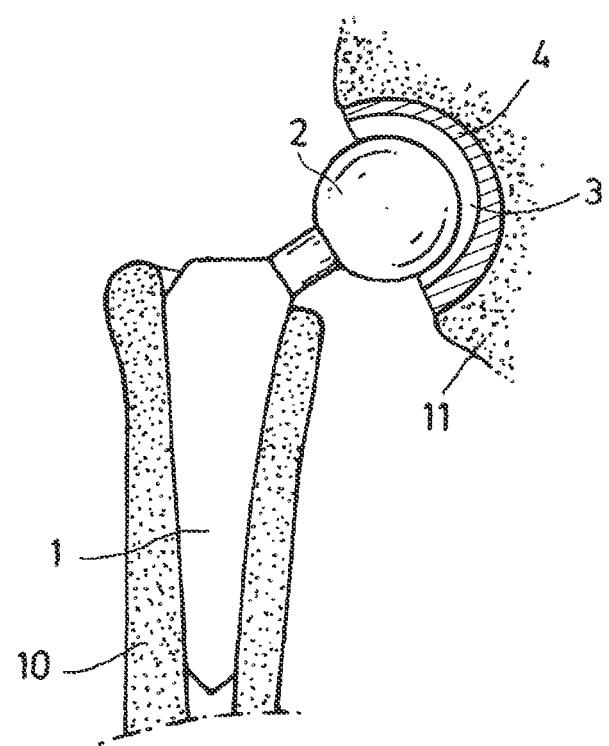

FIG. 6 shows a hip prosthesis having a shaft 1 coupled with a ball head 2 and a hip socket 4 coupled with a socket insert 3 in accordance with the invention. The shaft 1 and the his socket 4 are connected to the body of the patient as a result of growing into the femur 10 and pelvic bone 11 respectively and are carriers for the ball head 2 and socket insert 3 respectively. The ball head 2 is rotatably mounted in the hemispherical recess of the socket insert 3.

The invention claimed is:

1. A socket and socket insert for a hip-joint prosthesis, wherein the socket and the socket insert are formed asymmetrically in at least one of outer or inner geometries or a material composition thereof, wherein a partial element of material with differing rigidity and damping properties from those of the existing socket and socket insert is arranged in said socket and socket insert, wherein the socket insert has a hemispherical recess therein for receiving a ball head; wherein a partial element of material with differing rigidity and damping properties from those of the existing socket and the socket insert is arranged within the existing geometry of the socket.

2. A socket and socket insert according to claim 1, wherein axes of symmetry of the inner geometry and of the outer geometry of the socket and of the socket insert are displaced in parallel.

3. A socket and socket insert according to claim 1, wherein an axis of symmetry of an inner geometry is tilted in relation to the axis of symmetry of an outer geometry by an angle α.

4. A socket and socket insert according to claim 3, wherein the angle α lies in the range of 5 degrees<α<25 degrees.

5. A socket and socket insert according to claim 1, wherein the socket and the socket insert are composed of materials of differing rigidities and damping properties.

6. A socket and socket insert according to claim 1, wherein at least one of the socket and the socket insert have recesses on inner geometry or outer geometries thereof.

7. A socket and socket insert according to claim 1, wherein rigidities, damping properties or material are different along at least one of a socket axis or a socket-insert axis.

8. A socket for a hip-joint prosthesis, wherein said socket is formed asymmetrically in at least one of an outer geometry, inner geometry or material composition thereof, wherein the socket has a socket axis, wherein said hip-joint prosthesis has a socket insert and a shaft that can be coupled with a ball head, wherein the ball head can be inserted in a rotatable manner in the hemispherical recess of a socket insert, wherein the shaft can be implanted into a femur, and the socket insert can be implanted directly or by way of a hip socket into a pelvic bone; wherein the partial element of material with differing rigidity and damping properties from those of the existing socket and the socket insert is arranged within the existing geometry of the socket.

9. A socket according to claim 8, wherein axes of symmetry of an inner geometry and of an outer geometry of the socket is displaced in parallel.

10. A socket according to claim 8, wherein an axis of symmetry of the inner geometry is tilted in relation to the axis of symmetry of an outer geometry by an angle α.

11. A socket according to claim 10, wherein the angle α lies in the range of 5 degrees<α<25 degrees.

12. A socket according to claim 8, wherein the socket insert comprises materials of differing rigidities and damping properties.

13. A socket according to claim 8, wherein the socket has recesses on the inner geometry or outer geometry.

14. A socket according to claim 8, wherein at least one of rigidities, damping properties or a material are different along the socket axis.

15. A socket insert for a hip-joint prosthesis, wherein the socket insert is formed asymmetrically in at least one of an outer geometry, inner geometry or material composition thereof, wherein a partial element of material with differing rigidity and damping properties from those of the existing socket is arranged in the outer geometry of said socket insert, wherein the socket insert has a socket insert axis, a shaft that can be coupled with a ball head, wherein the ball head can be inserted in a rotatable manner in the hemispherical recess of the socket insert, wherein the shaft can be implanted into a femur, and the socket insert can be implanted directly or by way of a hip socket into a pelvic bone.

16. A socket insert according to claim 15, wherein axes of symmetry of an inner geometry and of an outer geometry of the socket insert are displaced in parallel.

17. A socket insert according to claim 15, wherein an axis of symmetry of an inner geometry is tilted in relation to an axis of symmetry of an outer geometry by an angle α.

18. A socket insert according to claim 17, wherein an angle α lies in the range of 5 degrees<α<25 degrees.

19. A socket insert according to claim 15, wherein the socket comprises materials of differing rigidities and damping properties.

20. A socket insert according to claim 15, wherein the socket insert has recesses on an inner geometry or an outer geometry thereof.

21. A socket insert according to claim 15, wherein a rigidity, damping property or a material are different along the socket-insert axis.

22. An assembly for a hip-joint prosthesis comprising:
a socket; and
a socket insert;
wherein the socket and the socket insert are formed asymmetrically in at least one of outer or inner geometries or a material composition thereof;
wherein a partial element of material with differing rigidity and damping properties from those of the existing socket and the socket insert is arranged within the existing geometry of the socket or the socket insert;
wherein the socket insert has a hemispherical recess therein for receiving a ball head.

23. A socket insert for a hip-joint prosthesis, wherein the socket insert is formed asymmetrically in at least one of an outer geometry, inner geometry or material composition thereof, wherein a partial element of material with differing rigidity and damping properties from those of the existing socket is arranged in the inner geometry of said socket insert, wherein the socket insert has a socket insert axis, a shaft that can be coupled with a ball head, wherein the ball head can be inserted in a rotatable manner in the hemispherical recess of the socket insert, wherein the shaft can be implanted into a femur, and the socket insert can be implanted directly or by way of a hip socket into a pelvic bone.

* * * * *

UNITED STATES PATENT AND TRADEMARK OFFICE
CERTIFICATE OF CORRECTION

PATENT NO. : 9,089,429 B2
APPLICATION NO. : 12/375699
DATED : July 28, 2015
INVENTOR(S) : Roman Preuss et al.

It is certified that error appears in the above-identified patent and that said Letters Patent is hereby corrected as shown below:

On the Title Page, Item (54) and in the Specification, column 1, lines 1-4, replace the title with the following:

-- ASYMMETRIC FORMATION OF SOCKETS AND/OR SOCKET INSERTS FOR THE MANIPULATION AND SUPPRESSION OF NATURAL FREQUENCIES --

Signed and Sealed this
Ninth Day of August, 2016

Michelle K. Lee
*Director of the United States Patent and Trademark Office*